(12) United States Patent
Xu et al.

(10) Patent No.: US 9,249,137 B2
(45) Date of Patent: Feb. 2, 2016

(54) DICARBOXIMIDE DERIVATIVES OF BERBAMINE, THE PREPARATION AND USE THEREOF

(75) Inventors: Rongzhen Xu, Hangzhou (CN); Frank Rong, Hangzhou (CN); Fuwen Xie, Longyan (CN); Hongxi Lai, Longyan (CN)

(73) Assignee: HANGZHOU BENSHENG PHARMACEUTICAL CO., LTD., Hangzhou, Zhejiang (CN)

( * ) Notice: Subject to any disclaimer, the term of this patent is extended or adjusted under 35 U.S.C. 154(b) by 329 days.

(21) Appl. No.: 13/819,111

(22) PCT Filed: Aug. 25, 2011

(86) PCT No.: PCT/CN2011/078905
§ 371 (c)(1),
(2), (4) Date: Feb. 26, 2013

(87) PCT Pub. No.: WO2012/025054
PCT Pub. Date: Mar. 1, 2012

(65) Prior Publication Data
US 2013/0158068 A1    Jun. 20, 2013

(30) Foreign Application Priority Data
Aug. 27, 2010  (WO) ................ PCT/CN2010/076423

(51) Int. Cl.
| | |
|---|---|
| *C07D 471/04* | (2006.01) |
| *C07D 401/14* | (2006.01) |
| *A61K 31/4745* | (2006.01) |
| *A61K 31/4375* | (2006.01) |
| *C07D 491/18* | (2006.01) |
| *A61P 35/02* | (2006.01) |
| *A61P 35/00* | (2006.01) |
| *C07D 491/16* | (2006.01) |

(52) U.S. Cl.
CPC ............ *C07D 471/04* (2013.01); *C07D 401/14* (2013.01); *C07D 491/16* (2013.01)

(58) Field of Classification Search
CPC .. C07D 401/12; C07D 401/14; C07D 471/04; A61K 31/4745; A61K 31/4375
See application file for complete search history.

(56) References Cited

U.S. PATENT DOCUMENTS
2010/0298369 A1   11/2010   Horne et al.
2014/0155423 A1*   6/2014   Horne et al. .................. 514/279

FOREIGN PATENT DOCUMENTS
CN   101273989   10/2008
JP   4099723 A   3/1992

OTHER PUBLICATIONS
International Search Report of PCT/CN2011/078905 mailed Dec. 1, 2011 (English translation).

* cited by examiner

*Primary Examiner* — Joseph Kosack
*Assistant Examiner* — Amanda L Aguirre
(74) *Attorney, Agent, or Firm* — McCarter & English, LLP; Steven G. Davis; Wei Song

(57) ABSTRACT

The present invention relates to a novel dicarboximide derivative of berbamine represented by formula I, including, but not limited to, a phthalimide derivative of berbamine and an aromatic heterocyclic dicarboximide derivative of berbamine, or a pharmaceutically acceptable salt thereof, to a process for preparation of the same, to a pharmaceutical composition comprising said compound and to use thereof in manufacture of an antitumor medicament.

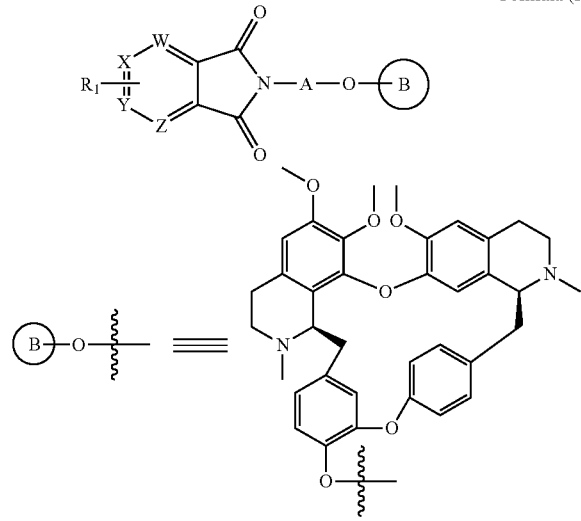

Formula (I)

16 Claims, No Drawings

DICARBOXIMIDE DERIVATIVES OF BERBAMINE, THE PREPARATION AND USE THEREOF

RELATED APPLICATIONS

This application is a 35 U.S.C. §371 national stage filing of International Application No. PCT/CN2011/078905, filed Aug. 25, 2011, which, in turn, claims priority to International Application No. PCT/CN2010/076423, filed Aug. 27, 2010.

TECHNICAL FIELD

The present invention belongs to the fields of natural medicine and pharmaceutical chemistry, and specifically relates to novel berbamine derivatives, particularly dicarboximide derivatives of berbamine, to process for the preparation of these compounds, a composition containing the compounds and their use in preparing an antitumor medicament.

BACKGROUND OF THE INVENTION

Berbamine (BBM), also known as 6,6',7-trimethoxy-2,2'-dimethylberbaman-12-ol, is a bi-benzyl isoquinoline alkaloid extracted from Chinese herbal plants of berberis. Due to its biological activities, many researchers are attracted to conduct extensive investigations on berbamine itself and its analogues.

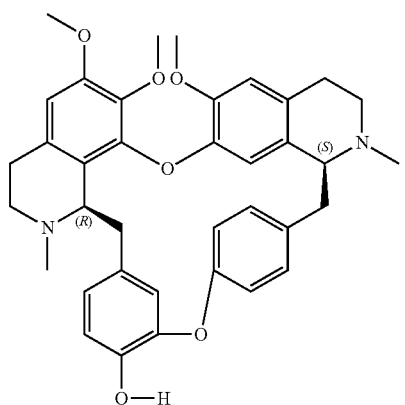

Berbamine
CAS: 478-61-5

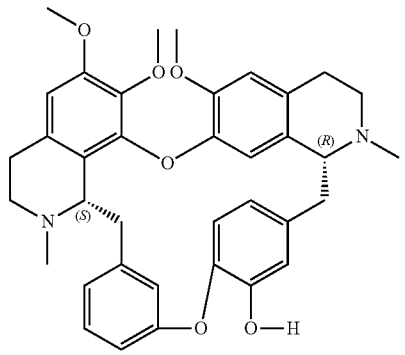

Oxyacanthine
CAS: 15352-74-6

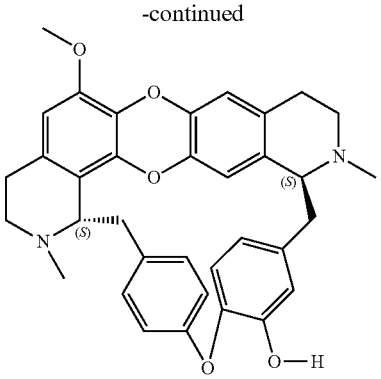

Cocsuline
CAS: 26279-88-9

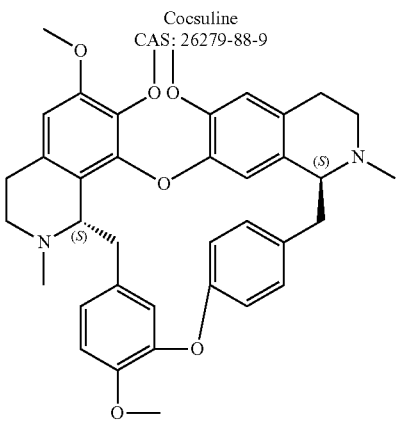

Tetrandrine
CAS: 518-34-3

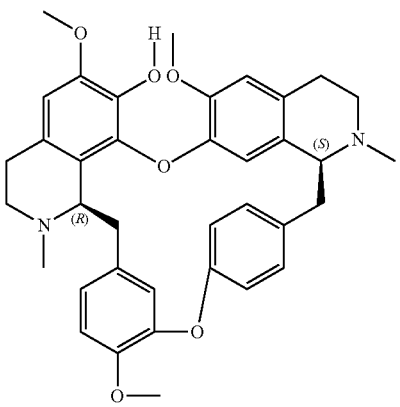

Fangchinoline
CAS: 436-77-1

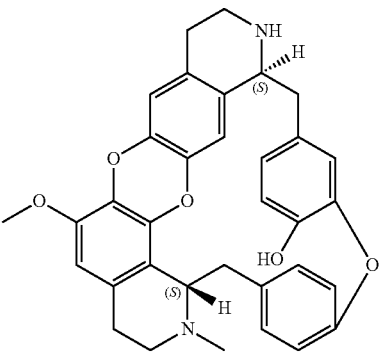

Cocsoline
CAS: 54352-70-4

-continued

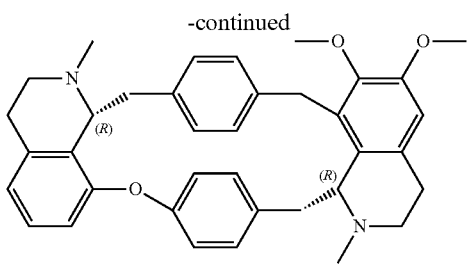

Cycleanine
Mol. Wt.: 560.73
CAS: 518-94-5

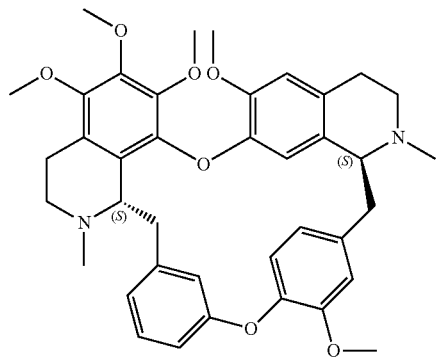

Thalrugosaminine
Mol. Wt.: 652.78
CAS: 22226-73-9

Berbamine and its Analogues

Berbamine has the effect of stimulating myeloid cell proliferation, improving the level of hematopoietic stem cell colony stimulating factor (GCSF), promoting the proliferation of bone marrow hematopoietic stem cells and myeloid progenitor cells and their differentiation to granulocytes, and promoting the proliferation of leukocytes [LIN Chuanrong, et al., The clinical observations on the treatment of chemotherapy-induced leukopenia with Shengbei'an (berbamine), Prepared Chinese Medicine, 1994, 16 (7): 29].

Berbamine inhibits the proliferation of prostate cancer PC-3 cells by introducing apoptosis and influencing the cell cycles in a time- and concentration-dependent manner [SUN Peng, et al., The effect of berbamine inducing apoptosis of prostate cancer PC-3 cells and the mechanism, Chinese Journal of Experimental Surgery, 2007, 24 (8): 957].

Berbamine exhibits obvious proliferation inhibition and clear apoptosis induction effects on the K562 cells in vitro, and has a time-concentration dependent relationship. In bodies of the tumor-bearing nude mice, berbamine also has significant inhibition effect on K562 cell growth, in particular can down-regulate the expression level of bcr/abl mRNA in tumor tissue cells [Wu Dong, et al., The experimental study of the actions of berbamine on K562 cells in vitro and in vivo, Journal of Chinese Experimental Hematology, 2005, 13 (3): 373].

Berbamine has effect of inhibiting cytotoxic T lymphocytes, and significantly promoting mice natural killer cell activity in vitro, and can induce relative high level of interleukin II (IL-2) in vitro and in vivo and avoid the toxic and adverse effects induced by large doses of IL-2 for treatment of tumor. It is demonstrated experimentally that berbamine has a good protective effect for immune system in mice against radiation damage [LIU Xin, et al., The immune regulation action of berbamine on BALB/C mice, Journal of China Medical University, 1996, 25 (3): 229; LUO Chongnian, et al., The inhibition of berbamine on mice splenocytes cytotoxic T lymphocyte activity, Chinese Journal of Pharmacology and Toxicology, 1995, 9 (2): 159-160; G E Mingzhu, et al., The experimental study of immune protection action of berbamine on irradiated mice, Journal of Immunology, 1998, 14 (4): 238].

There also are the studies and reports on the mechanism of berbamine inducing apoptosis of human leukemia Jurkat cells. The results show that, berbamine can selectively inhibit the apoptosis of human leukemia Jurkat cells, make the cell cycle arrested in S phase, and increase the caspase-3 protein expression of the cells. And as the increase of drug concentration from 0.5 ug/mL to 10 ug/mL, the cell viability rate was reduced from 93.69% to 14.85%, and berbamine in this action concentration range was found having no obvious cytotoxicity on normal human peripheral blood leucocytes [DONG Zhiyu, et al., The experimental study of berbamine on inducing apoptosis of human leukemia Jurkat cells, Chinese Tumor, 2007, 16 (9): 722].

Berbamine hydrochloride tablet has been approved for marketing in China, and is used for treating leukopenia of various causes, including prevention of leukocytopenia after radiotherapy or chemotherapy of cancer.

There are also reports about the inhibiting effect of berbamine on cell proliferation. For example, berbamine and some of berbamine derivatives have significant inhibiting effect on brain malignant glioma cells, human cervical carcinoma cells, ascites carcinoma cells and melanoma cells [ZHANG Jinhong, et al., The influence of the structures of the berbamine and its derivatives on cervical carcinoma (CHeLa) cells proliferation, Acta Scientiarum Naturalium University Nankaiensis, 1996, 29 (2): 89; ZHANG Jinhong, et al., The influence of the berbamine and its derivatives on malignant melanoma cell proliferation, Chinese Herbal Medicine, 1997, 28 (8): 483; ZHANG Jinhong, et al., The preliminary exploration of the in vivo antitumor effect of the berbamine derivatives (EBB), Chinese Herbal Medicine, 1998, 29 (4): 243; DUAN Jiangyan et al., The influence of berbamine compounds on calmodulin protein level within melanoma cells, Chinese Herbal Medicine, 2002, 33 (1): 59]. [O-(4-ethoxy)-butyl]-berbamine (EBB) is a highly specific CaM antagonist, with a specific coefficient of 6.5-fold higher than that of berbamine. EBB induces apoptosis of lung cancer cells and maintains the normal cell biological functions of main organs at the same time [DUAN Jiangyan, et al., The preliminary exploration of [O-(4-ethoxy)-butyl]-berbamine for induction of lung cancer cell apoptosis, Journal of Shanxi Normal University (NATURAL SCIENCE EDITION), 2001, 15 (4): 55]. Another berbamine derivative is O-Dansyl berbamine (DB) which comprises a hydrophobic fluorescent moiety. DB exhibits the inhibitory activity on the red cell membrane CaM-independent $Ca^{2+}+Mg^{2+}$ ATPase that was 25-fold stronger than that of berbamine DB has a significant inhibitory effect on intracellular granzyme phosphodiesterase activity, and there was a relation between the dose and the activity. In addition, it was also found that the effect of DB on lung cancer cells was stronger than that of berbamine, whereas the toxicity of DB on human embryonic lung cell was lower than that of berbamine. The inhibition of DB on lung cancer cells is not only related to the inhibition of oncogene, but also related to the control of the inactivated tumor suppressor genes [ZHANG Jinhong, et al., The influence of the calmodulin antagonist O-Dansyl berbamine on phosphodiesterase and pulmonary cell proliferation, Acta Scientiarum Naturalium University Nankaiensis, 2001, 34 (3): 64].

The present inventors have described in patent No. CN 101273989A the use of a class of berbamine derivatives, mainly involved benzoyl and benzyl derivatives, for preparation of an antitumor drug.

So far, the reported berbamine compounds can only transiently inhibit tumor cell growth, but cannot completely removed the tumor, especially hematological malignancies such as leukemia, multiple myeloma and lymphoma, and solid tumors such as liver cancer, lung cancer, breast cancer, prostate cancer, osteosarcoma and the like. Obviously, the research and development of berbamine derivatives with higher antitumor activities are still to be conducted.

SUMMARY OF THE INVENTION

One object of the present invention is to provide novel dicarboximide derivatives of berbamine of formula (I):

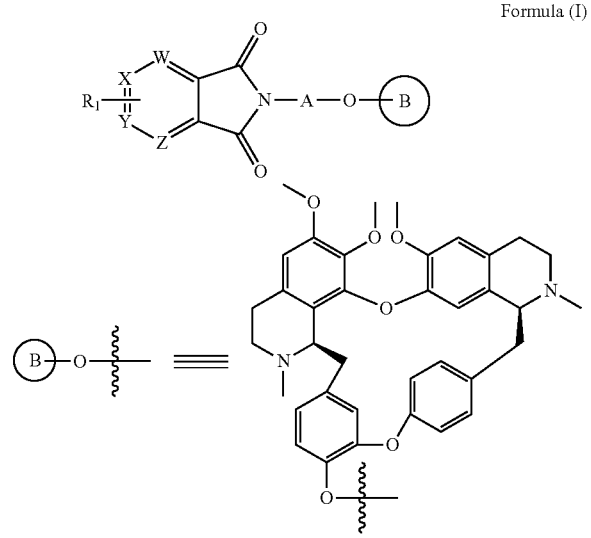

Formula (I)

wherein, $R_1$ is selected from H, halogen, amino, nitro, cyano, hydroxyl, mercapto, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, substituted or unsubstituted $C_3$-$C_7$ cycloalkyl;

A is selected from a linear or branched, substituted or unsubstituted alkylene —$(CH_2)_n$—, optionally being interrupted by a heteroatom selected from the group consisting of O, N and S, and wherein n is an integer from 1 to 15; W, X, Y and Z are independently selected from substituted or unsubstituted methine CH, methylene $CH_2$ and a heteroatom selected from the group consisting of O, N and S, and wherein at least two of W, X, Y and Z are CH or $CH_2$;

The "substituted" means a substitution by a substituent selected from the group consisting of halogen, amino, nitro, cyano, hydroxyl and mercapto group;

or a pharmaceutically acceptable salt thereof.

Preferably, in formula (I), W=X=Y=Z=CH.

Preferably, in formula (I), A is an unsubstituted alkylene —$(CH_2)_n$—.

In a preferable embodiment, the present invention provides the phthalimide derivatives of berbamine of formula (I-a):

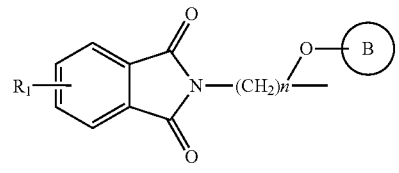

Formula (I-a)

wherein each group is defined same as in formula (I).

When there is one or two heteroatoms among W, X, Y and Z, and A is an unsubstituted alkylene —$(CH_2)_n$—, the present invention provides the aromatic heterocyclic dicarboximide derivatives of berbamine of formula (I-b):

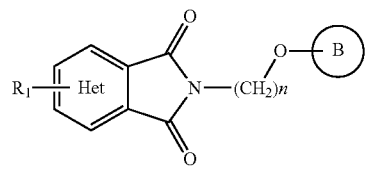

Formula (I-b)

wherein each group is defined same as in formula (I).

Another object of the present invention is to provide a process for preparing the compounds of formula (I):

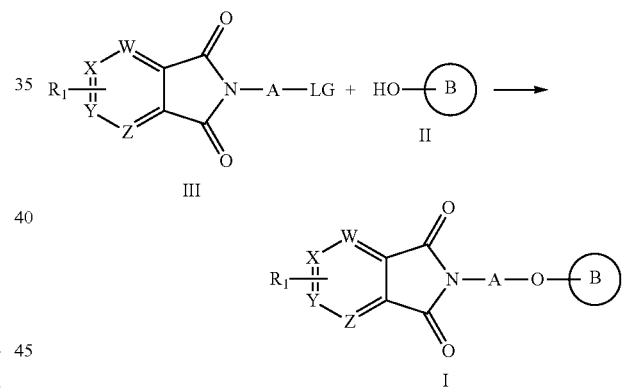

wherein the compound of formula (I) is prepared by reacting the compound of formula (III) with the compound of formula (II), wherein $R_1$, A, W, X, Y, Z are defined same as in formula (I); and LG is a leaving group which may be, but not limited to, halogen, sulfonate group, etc.

Another object of the present invention is to provide a pharmaceutical composition comprising a compound of the present invention, said pharmaceutical composition comprising at least one compound of the present invention and optionally a pharmaceutically acceptable excipient.

Another object of the present invention is to provide use of a compound of the present invention or a pharmaceutical composition comprising the compound of the present invention in manufacture of a medicament, especially an antitumor medicament. Accordingly, the present invention provides a method for treating a patient suffering from tumor, comprising administrating to the patient in need thereof an effective amount of at least one compound of the present invention. Said tumor is particularly selected from leukemia, multiple myeloma, lymphoma, liver cancer, gastric cancer, breast cancer, cholangiocellular carcinoma, pancreatic cancer, lung cancer, large intestine carcinoma, osteosarcoma, melanoma, prostate cancer, and so on.

The present invention also relates to the compound of the present invention for treating tumor.

DETAILED DESCRIPTION OF THE INVENTION

The present invention relates to a novel dicarboximide derivative of berbamine of formula (I):

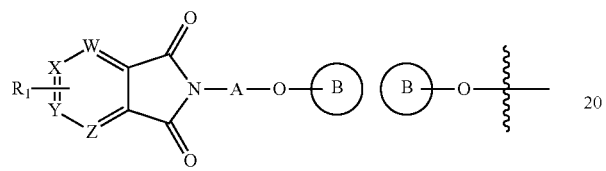

Formula (I)

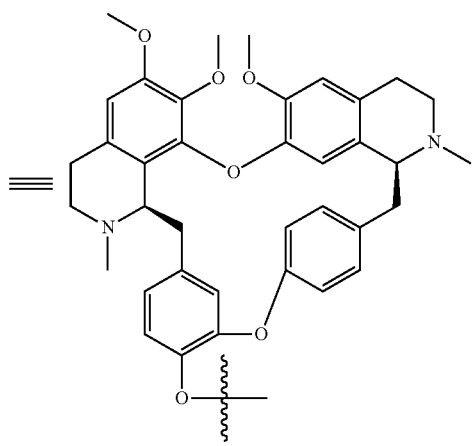

wherein, $R_1$ is selected from H, halogen, amino, nitro, cyano, hydroxyl, mercapto, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, substituted or unsubstituted $C_3$-$C_7$ cycloalkyl;

A is selected from a linear or branched, substituted or unsubstituted alkylene $—(CH_2)_n—$, optionally being interrupted by a heteroatom selected from the group consisting of O, N and S, and wherein n is an integer from 1 to 15; W, X, Y and Z are independently selected from substituted or unsubstituted methine CH, methylene $CH_2$ and a heteroatom selected from the group consisting of O, N and S, and wherein at least two of W, X, Y and Z are CH or $CH_2$;

The "substituted" means a substitution by a substituent selected from the group consisting of halogen, amino, nitro, cyano, hydroxyl and mercapto group;

or a pharmaceutically acceptable salt thereof.

When W=X=Y=Z=CH, and A is an unsubstituted alkylene $—(CH_2)_n—$, the present invention provide a phthalimide derivative of berbamine of formula (I-a):

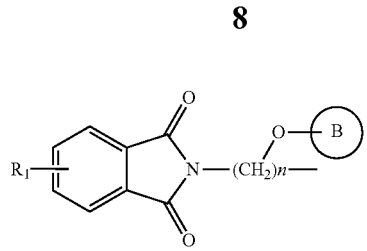

Formula (I-a)

When there are one or two heteroatoms in W, X, Y and Z, and A is an unsubstituted alkylene $—(CH_2)_n—$, the present invention provides an aromatic heterocyclic dicarboximide derivative of berbamine of formula (I-b):

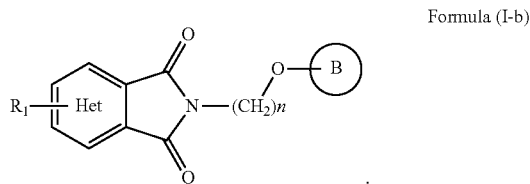

Formula (I-b)

In one embodiment, the present invention relates to a compound of formula (I-a), wherein n is an integer of 1-15; but when $R_1$ is H, n is not 2.

In one embodiment, the present invention relates to a compound of formula (I-a), wherein n is an integer of 1-15; but when $R_1$ is H, n is not 3.

In one embodiment, the present invention relates to a compound of formula (I-a), wherein n is an integer of 1-10.

In one embodiment, the present invention relates to a compound of formula (I-a), wherein n is an integer of 1-10; but when $R_1$ is H, n is not 2.

In one embodiment, the present invention relates to a compound of formula (I-a), wherein n is an integer of 1-10; but when $R_1$ is H, n is not 3.

In one embodiment, the present invention relates to a compound of formula (I-a), wherein n is an integer of 1-8.

In one embodiment, the present invention relates to a compound of formula (I-a), wherein n is an integer of 1-8; but when $R_1$ is H, n is not 2.

In one embodiment, the present invention relates to a compound of formula (I-a), wherein n is an integer of 1-8; but when $R_1$ is H, n is not 3.

In one embodiment, the present invention relates to a compound of formula (I-a), wherein n is an integer of 1-7.

In one embodiment, the present invention relates to a compound of formula (I-a), wherein n is an integer of 1-7; but when $R_1$ is H, n is not 2.

In one embodiment, the present invention relates to a compound of formula (I-a), wherein n is an integer of 1-7; but when $R_1$ is H, n is not 3.

In one embodiment, the present invention relates to compounds of formulae (I-a) and (I-b), wherein n is an integer of 1, 2, 3, 4, 5, 6, 7, 8, 9, 10, 11, 12, 13, 14 or 15, or n is an integer within a range with any two of these number as end value, e.g., n is within a range of 4-7, 4-8, 4-9, 4-10, 4-11, 4-12, 4-13, 4-14, 4-15, 5-7, 5-8, 5-9, 5-10, 5-11, 5-12, 5-13, 5-14, 5-15, etc.

In one embodiment, the present invention relates to a compound of formula (I), wherein $R_1$ is selected from H, $C_1$-$C_6$ alkoxy, halogenated $C_1$-$C_6$ alkoxy, $C_1$-$C_6$ alkylthio, halogenated $C_1$-$C_6$ alkylthio, $C_1$-$C_6$ alkyl, halogenated $C_1$-$C_6$ alkyl, $C_3$-$C_7$ cycloalkyl, halogenated $C_3$-$C_7$ cycloalkyl, halogen, nitro, cyano, and amino optionally substituted with one or two $C_1$-$C_6$ alkyl.

In one embodiment, the present invention relates to a compound of formula (I), wherein $R_1$ is selected from H, $C_1$-$C_6$ alkoxy, $C_1$-$C_6$ alkylthio, $C_1$-$C_6$ alkyl, $C_3$-$C_7$ cycloalkyl, halogen, nitro, cyano and amino optionally substituted with one or two $C_1$-$C_6$ alkyl.

In one embodiment, the present invention relates to a compound of formula (I), wherein $R_1$ is selected from H, $C_1$-$C_6$ alkoxy, $C_1$-$C_6$ alkyl, $C_3$-$C_7$ cycloalkyl, or halogen.

In one embodiment, the present invention relates to a compound of formula (I), wherein $R_1$ is H, $C_1$-$C_3$ alkoxy, $C_1$-$C_3$ alkyl, or $C_5$-$C_6$ cycloalkyl.

In one embodiment, the present invention relates to a compound of formula (I), wherein $R_1$ is H, methoxy, or methyl.

In one embodiment, the present invention relates to a compound of formula (I), wherein $R_1$ is H.

In one embodiment, the present invention relates to a compound of formula (I), wherein $R_1$ is selected from substituted or unsubstituted $C_1$-$C_6$ alkyl, said "substituted" means a substitution by a substituent selected from the group consisting of halogen, amino, nitro, cyano, hydroxyl and mercapto group.

In one embodiment, the present invention relates to a compound of formula (I), wherein $R_1$ is selected from substituted or unsubstituted $C_1$-$C_6$ alkoxy, said "substituted" means a substitution by a substituent selected from the group consisting of halogen, amino, nitro, cyano, hydroxyl and mercapto group.

In one embodiment, the present invention relates to a compound of formula (I), wherein $R_1$ is selected from substituted or unsubstituted $C_1$-$C_6$ alkylthio, said "substituted" means a substitution by a substituent selected from the group consisting of halogen, amino, nitro, cyano, hydroxyl and mercapto group.

In one embodiment, the present invention relates to a compound of formula (I), wherein $R_1$ is selected from substituted or unsubstituted $C_1$-$C_6$ alkylamino, said "substituted" means a substitution by a substituent selected from the group consisting of halogen, amino, nitro, cyano, hydroxyl and mercapto group.

In one embodiment, the present invention relates to a compound of formula (I), wherein $R_1$ is selected from substituted or unsubstituted $C_3$-$C_7$ cycloalkyl, said "substituted" means a substitution by a substituent selected from the group consisting of halogen, amino, nitro, cyano, hydroxyl and mercapto group.

In one embodiment, the present invention relates to a compound of formula (I), wherein the position of $R_1$ substituent is α-position.

In one embodiment, the present invention relates to a compound of formula (I), wherein the position of $R_1$ substituent is β-position.

In one embodiment, the present invention relates to a compound of formula (I), wherein the position of $R_1$ substituent is α- and β-position.

In one embodiment, the present invention relates to a compound of formula (I), wherein A is selected from a linear or branched, substituted or unsubstituted alkylene —$(CH_2)_n$—, optionally being interrupted by a heteroatom selected from the group consisting of O, N and S, wherein n is an integer from 1 to 15.

In another embodiment, the present invention particularly relates to the following preferable compound of formula (I) or a pharmaceutically acceptable salt thereof:

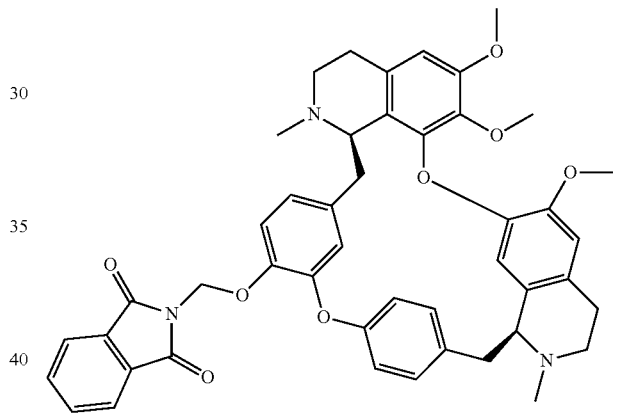

12-O-((1,3-dioxo-isoindolin-2-yl)-methyl)-berbamine (Compound BS-BE-001)

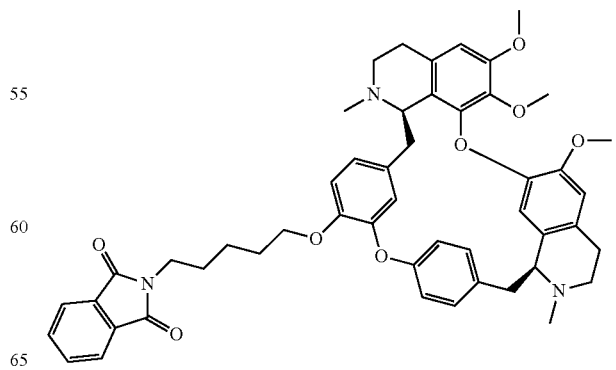

12-O-(5-(1,3-dioxo-isoindolin-2-yl)-pentyl)-berbamine (Compound BS-BE-002)

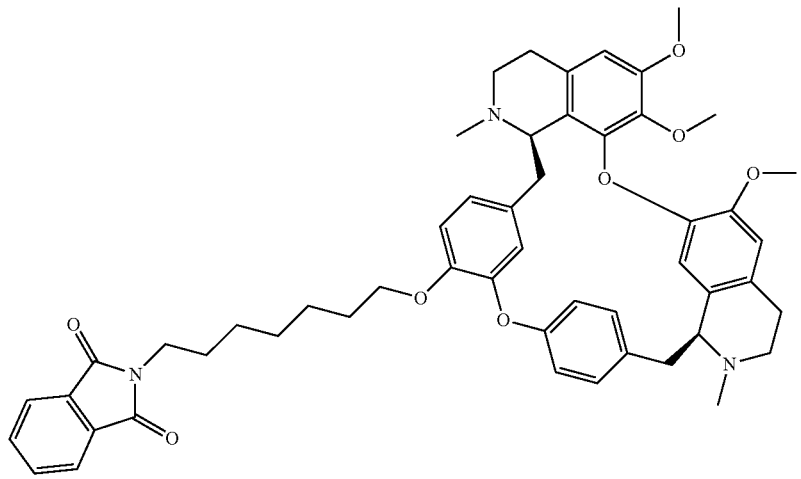 [SMILES: COc1cc2c3cc1Oc1c(OC)c(OC)cc4c1[C@@H](Cc1ccc(OCCCCCCCN5C(=O)c6ccccc6C5=O)c(c1)Oc1ccc(cc1)C[C@@H]3N(C)CC2)N(C)CC4]

12-O-(7-(1,3-dioxo-isoindolin-2-yl)-heptyl)-berbamine (Compound BS-BE-003)

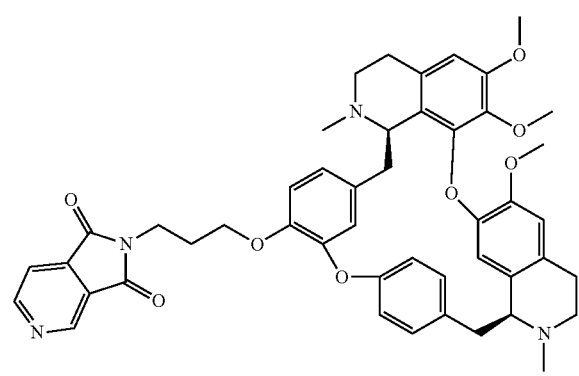 [SMILES: COc1cc2c3cc1Oc1c(OC)c(OC)cc4c1[C@@H](Cc1ccc(OCCCN5C(=O)c6ccncc6C5=O)c(c1)Oc1ccc(cc1)C[C@@H]3N(C)CC2)N(C)CC4]

12-O-(3-(3,4-pyridine-dicarboximide)-propyl)-berbamine (Compound BS-BE-004).

The present invention relates to the compounds of Formula (I) in the form of a salt, a solvate, a hydrate, an adduct, a complex, a polymorph or a prodrug thereof.

As used herein, the term "$C_1$-$C_6$ alkyl" refers to a straight or branched hydrocarbon group containing 1 to 6 carbon atoms. Examples of $C_1$-$C_6$ alkyl include, but not limited to, methyl, ethyl, n-propyl, isopropyl, tert-butyl, n-pentyl and n-hexyl.

The term "$C_1$-$C_6$ alkoxy" refers to an —O—$C_1$-$C_6$ alkyl.

The term "$C_1$-$C_6$ alkylthio" refers to an —S—$C_1$-$C_6$ alkyl.

The term "$C_3$-$C_7$ cycloalkyl" refers to a hydrocarbon radical of saturated cyclic 3-7 membered monocyclic system. Representative examples of $C_3$-$C_7$ cycloalkyl may be cyclopropyl, cyclobutyl, cyclopentyl, cyclohexyl, and cycloheptyl.

The term "halogen", "halo" or "hal" means fluorine, chlorine, bromine or iodine.

The "substituent" of the present invention can be one or more, depending on the number of hydrogen on the substituted group and stability of the combination of chemical groups. When there are multiple substituents, they can be same or different.

As used herein, the term "a pharmaceutically acceptable salt of a compound of formula (I)" means an organic acid addition salt formed with an organic acid which creates a pharmaceutically acceptable anion, the examples includes but not limited to, tosylate, methanesulfonate, malate, acetate, citrate, malonate, tartrate, succinate, benzoate, ascorbate, lactate, α-ketoglutarate, and α-glycerophosphate. Suitable inorganic salts may also be formed, including but not limited to, hydrochlorate, sulfate, nitrate, bicarbonate and carbonate, phosphate, hydrobromate, hydriodate salts and the like.

A pharmaceutically acceptable salt may be obtained using standard procedures well known in the art, for example by reacting a sufficient amount of a basic compound with a suitable acid providing a pharmaceutically acceptable anion.

As used herein, the term "polymorph" means a solid crystalline form of a compound of the present invention or a complex thereof. Various polymorphs of one same compound may exhibit different physical, chemical and/or spectroscopic properties. The different physical properties include, but not limited to, stability (e.g., thermal or light), compressibility and density (which are important for formulation and manufacture of the product), and dissolution rate (which may affect its bioavailability). Differences in stability may result in a change in chemical reactivity (e.g., differential oxidation, such that a dosage form comprised of one polymorph discolors more rapidly than that comprised of another polymorph) or mechanical properties (e.g., in storage, a kinetically favored polymorph in tablet crumble converts to a more thermodynamically stable polymorph) or both (e.g., tablets composed of one polymorph are more susceptible to breakdown at high humidity). Different physical properties of various polymorphs may affect their processing. For example, one polymorph may be more likely to form a solvate or may be more difficult to filter out or remove impurities by washing than another one due to, for example, their particle shape or size distribution.

As used herein, the term "hydrate" means a compound of the present invention or a salt thereof further comprising a stoichiometric or non-stoichiometric amount of water bound via non-covalent intermolecular forces.

As used herein, the term "prodrug" means a derivative of a compound of the invention that can provide a compound of this invention under a biological condition (in vitro or in vivo) via a hydrolyzation, oxidization, or other reactions, unless otherwise indicated. A prodrug may only become active upon such a reaction under a biological condition, or may have activities in its unreacted form. Typically, a prodrug can be prepared using well-known methods, such as those described in BURGER'S MEDICINAL CHEMISTRY AND DRUG DISCOVERY (1995) 172-178, 949-982 (Manfred E. Wolff ed., 5$^{th}$ ed).

The berbamine ring moiety in the compounds of the present invention has the stereochemical structure represented by the structural formula I. The stereochemical definitions and conventions used herein generally follow MCGRAW-HILL DICTIONARY OF CHEMICAL TERMS (S. P. Parker, Ed., McGraw-Hill Book Company, New York, 1984); and ELIEL, E. AND WILEN, S., STEREOCHEMISTRY OF ORGANIC COMPOUNDS (John Wiley & Sons, Inc., New York, 1994). Many organic compounds are present in optically active forms, i.e., they have the ability to rotate a plane of plane-polarized light.

The terms "treatment," "treating," "treat," and the like used herein refer generally to obtaining a desired pharmacological and/or physiological effect. The effect may be prophylactic in terms of completely or partially preventing a disease or symptoms thereof and/or may be therapeutic in terms of partial or complete stabilization or cure of a disease and/or adverse effects caused by the disease. "Treatment" as used herein covers any treatment of a disease in a subject, including: (a) preventing the disease or symptoms from occurring in a subject who is predisposed to the disease or symptoms but has not yet been diagnosed as having it; (b) inhibiting the symptoms of a disease, i.e., arresting its development; or (c) relieving the symptoms of a disease, i.e., causing regression of the disease or symptoms.

The compounds of the present invention can be prepared through a conventional organic chemistry synthesis process. For example, the present invention relates to a process for preparing the compound of formula (I):

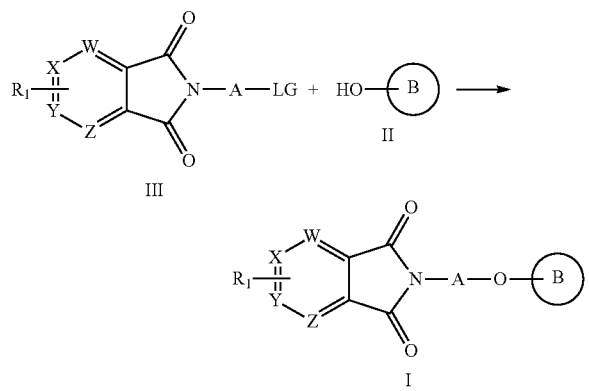

wherein, the compound of formula (I) is prepared by reacting a compound of formula (III) with a compound of formula (II), wherein A, B, W, X, Y, Z and $R_1$ are defined same as in formula (I) above; and LG is a leaving group which can be, but not limited to, halogen (such as chlorine, bromine, iodine), sulfonate (such as methyl sulfonate, p-toluene sulfonate) group, etc.

This reaction is generally carried out in the presence of a base which may be, but not limited to, sodium, sodium hydride, sodium hydroxide or potassium hydroxide, and so on.

This reaction is generally carried out in a solvent. The useful solvents include, but not limited to, a polar aprotic solvent such as dimethyl sulfoxide (DMSO), dimethyl formamide (DMF) or hexamethyl phosphoramide (HMPT), etc.

The reaction temperature is generally from 0° C. to room temperature, and varies depending on the used reaction materials and base.

The compound of formula (II) is berbamine as a natural product obtained by separation and extraction, which is commercially available.

The appropriate examples of the compound of formula (III) include N-(2-chloroethyl)-phthalimide, N-(5-bromoamyl)-phthalimide, N-(7-bromoheptyl)-phthalimide, N-(3-bromopropyl)-pyridine-dicarboximide, etc. which are appropriately substituted or unsubstituted on the benzene ring.

The compound of formula (III) can be synthesized by conventional processes, for example, by reacting an optionally substituted phthalimide or a pyridine-dicarboximide with an alkylene dihalide (such as alkylene dichloride or alkylene dibromide) or an alkylene disulfonate (such as methylsulfonate or toluenesulfonate) in the presence of a base. The reactants alkylene dihalide or alkylene disulfonate can be prepared by a halogenation or esterification reaction of an alkylene glycol.

Conventional chemical conversion processes may be used to practice this invention. One skilled person in the art would be capable to determine suitable chemical agents, solvents, protecting groups, and reaction conditions for these chemical conversions. Relevant information are described, for example, in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

Protecting groups refer to the groups that, upon being attached to an active moiety (e.g., a hydroxyl or amino group), prevent the moiety from interference in a subsequent reaction and, after the reaction, can be removed through a conventional method. Examples of a hydroxyl protecting group include, but not limited to, alkyl, benzyl, allyl, trityl (also known as triphenylmethyl), acyl (e.g., benzoyl, acetyl, or HOOC—X"—CO—, wherein X" is alkylidene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of an amino protecting group include, but not limited to, alkoxycarbonyl, alkanoyl, aryloxycarbonyl, aryl-substituted alkyl and the like. Hydroxyl and amino protecting groups have been discussed in T. W. Greene and P. G. M. Wuts, Protective Groups in Organic Synthesis, 2 nd. Ed., John Wiley and Sons (1991). All hydroxyl and amino protecting groups can be removed by a conventional method after the reaction.

The present invention also provides a pharmaceutical composition comprising a compound of formula (I) of the present invention.

The present invention provides such a pharmaceutical composition that it comprises at least one compound of formula (I) of the present invention above and optionally a pharmaceutically acceptable excipient.

The methods for preparing various pharmaceutical compositions having a certain amount of active components are known or will be apparent to those skilled in the art in light of this disclosure. As described in REMINGTON'S PHARMACEUTICAL SCIENCES, Martin, E. W., ed., Mack Publishing Company, 19 th ed. (1995), the methods for preparing such pharmaceutical compositions include incorporation of other suitable pharmaceutical excipients, carriers, diluents, etc.

The pharmaceutical preparations of the present invention are produced by known methods, including routine mixing, dissolving, or lyophilizing processes.

The compounds of the present invention may be formulated into a pharmaceutical composition and administered to a patient in a route suitable for the selected administration manner, e.g., orally or parenterally (by an intravenous, intramuscular, topical or subcutaneous route).

Thus, the present compounds may be systemically administered, e.g., orally, in conjugation with a pharmaceutically acceptable carrier such as an inert diluent or an assimilable edible carrier. They may be enclosed in hard or soft gelatin capsules, or may be compressed into tablets. For oral therapeutic administration, the active compound may be combined with one or more excipients and may be taken in a form of ingestible tablet, buccal tablet, troche, capsule, elixir, suspension, syrup, wafer, and the like. Such a composition and preparation should contain at least 0.1% of the active compound. This proportion of the compositions and preparations may, of course, vary and may conveniently be from about 1% to about 99% by the weight of a given unit dosage form. The active compound is present in such a therapeutically useful composition in an amount such that an effective dosage level is achieved.

A tablet, troche, pill, capsule and the like may also comprises a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, wintergreen oil, or cherry flavor. When being a capsule as the unit dosage form, it may comprise, in addition to the above material types, a liquid vehicle such as a vegetable oil or polyethylene glycol. Various other materials may be present as coatings or otherwise modify the physical form of the solid unit dosage form. For instance, a tablet, pill, or capsule may be coated with gelatin, wax, shellac or sugar, etc. A syrup or elixir may contain an active compound, a sweetening agent such as sucrose or fructose, a preservative such as methylparaben or propylparaben, a dye and a flavoring agent such as cherry or orange flavor. Of course, any materials used in preparing any unit dosage form should be pharmaceutically acceptable and substantially non-toxic in the amounts employed. In addition, the active compound may be incorporated into a sustained-release preparation and device.

The active compound may also be administered by infusion or injection intravenously or intraperitoneally. An aqueous solution of the active compound or its salt may be prepared, optionally mixed with a nontoxic surfactant. A dispersion can also be prepared in glycerol, liquid polyethylene glycol, triacetin, and a mixture thereof and in an oil. Under ordinary storage and use conditions, these preparations contain a preservative to prevent the growth of microorganisms.

The pharmaceutical dosage forms suitable for injection or infusion can include a sterile aqueous solution or dispersion or a sterile powder comprising the active ingredient (optionally encapsulated in liposomes) which are adapted for an extemporaneous preparation of a sterile injectable or infusible solution or dispersion. In all cases, the final dosage form must be sterile, liquid and stable under the manufacture and storage conditions. The liquid carrier or vehicle may be a solvent or a liquid dispersion medium comprising, for example, water, ethanol, a polyol (for example, glycerol, propylene glycol, liquid polyethylene glycol, and the like), a vegetable oil, a nontoxic glyceryl ester, and a suitable mixture thereof. The proper fluidity can be maintained, for example, by formation of liposomes, by maintenance of the required particle size in the case of dispersion or by the use of a surfactant. The prevention of microorganism action can be achieved by various antibacterial and antifungal agents, such as parabens, chlorobutanol, phenol, sorbic acid, thimerosal, and the like. In many cases, it will be preferable to include an isotonic agent, such as a sugar, a buffer agent or sodium chloride. Prolonged absorption of an injectable composition can be obtained by the use of a composition of the agents for delaying absorption, for example, aluminum monostearate and gelatin.

A sterile injectable solution is prepared by combining the active compound of a required amount in a suitable solvent with various additional components as listed above as required, followed by filter sterilization. In the case of sterile powder for preparation of a sterile injectable solution, the preferred preparation process is the vacuum drying and lyophilization techniques, which yield a powder of the active ingredient plus any additional desired ingredient present in the previously sterile-filtered solution.

Useful solid carriers include finely divided solids (such as talc, clay, microcrystalline cellulose, silica, alumina and the like). Useful liquid carriers include water, ethanol or ethylene glycol or a water-ethanol/ethylene glycol mixture, in which the compound of the present invention can be dissolved or dispersed at an effective level optionally with the aid of a non-toxic surfactant. An adjuvant such as a flavour and an additional antimicrobial agent can be added to optimize the properties for a given application.

A thickener material (such as a synthetic polymer, a fatty acid, a fatty acid salt and ester, a fatty alcohol, a modified cellulose or a modified mineral) can also be used with a liquid carrier to form a spreadable paste, gel, ointment, soap and the like for application directly to the skin of a user.

The treatment required amount of the compound or an active salt or derivative thereof will vary depending not only on the selected particular salt but also on the administration route, the nature of the condition to be treated and the age and condition of the patient, and will be ultimately determined at the discretion of the attendant physician or clinician.

The above formulations can present in a unit dosage form which is a physically discrete unit containing a unit dosage suitably administrating to a human or other mammalians The unit dosage form may be a capsule or a tablet, or a plurality of capsules or tablets. Depending upon the intended particular treatment, the amount of the active ingredient in a unit dosage form can be varied or adjusted in the range of about 0.1 mg to about 1,000 mg or more.

The present invention also provides the use of a compound according to the present invention or a pharmaceutical composition comprising the compound of the present invention in manufacture of a medicament, especially an antitumor medicament. Accordingly, the present invention provides a method for treating a patient suffering from tumor, comprising administrating to the patient in need thereof an effective amount of at least one compound of the present invention. The berbamine derivative of the present invention or a pharmaceutically acceptable salt thereof can be used, for example, for treatment of leukemia, multiple myeloma, lymphoma, liver cancer, gastric cancer, breast cancer, cholangiocellular carcinoma, pancreatic cancer, lung cancer, carcinoma of large intestine, osteosarcoma, melanoma, human cervical cancer, glioma, nasopharyngeal carcinoma, laryngeal carcinoma, esophageal cancer, middle ear tumor, prostate cancer, and so on.

In the following examples, the present invention will be explained more detailedly. However, it should be understood that the following examples are intended to illustrate the present invention but not to limit the scope of the present invention in any way.

The raw chemicals used in the following examples are commercially available or may be obtained by a synthesis method well known in the art.

Example 1

The Synthesis of Compound (BS-BE-001)

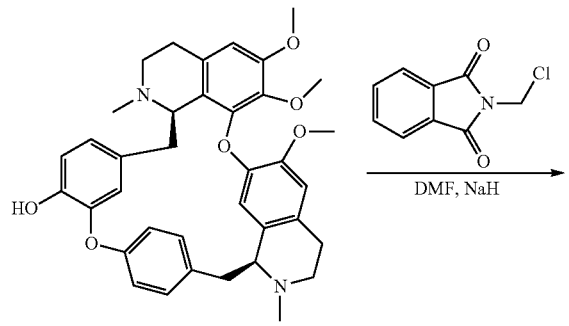

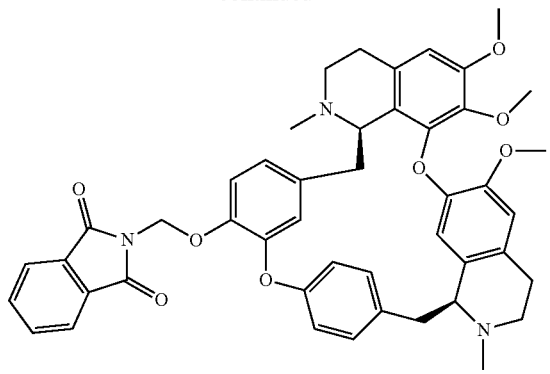

Under a protective nitrogen atmosphere, sodium hydride (NaH, 48 mg, 1.2 mmol) is added into a solution of berbamine dihydrochloride (205 mg, 0.3 mmol) in N,N-dimethyl formamide (5 ml) at 0° C., after being stirred for 1 hour, 2-chloromethyl-isoindoline-1,3-dione (88 mg, 0.45 mmol) is added therein. The reaction solution is heated to 80° C. overnight. Then the reaction mixture is evaporated under vacuum, and purified by a preparative thin layer chromatography to give white or pale yellow compound (BS-BE-001) (11.5 mg, 5.0%).

LC/MS m/z: M+1 768.3 100% (purity).

$^1$H NMR (CDCl$_3$) δ: 7.88~7.865 (dd, 2H, J=6.0 Hz, 5.5 Hz), 7.74~7.732 (dd, 2H, J=5.5 Hz, 6.0 Hz), 7.264 (s, 1H), 7.01~96.998 (dd, 1H, J=8.5 Hz, 8.0 Hz), 6.919~6.903 (d, 1H, J=7.5 Hz), 6.71~6.698 (d, 1H, J=7.5 Hz), 6.62~6.614 (m, 1H), 6.527 (s, 1H), 6.420~6.385 (m, 1H), 6.266 (s, 1H), 5.954 (s, 1H), 5.766~5.717 (m, 2H), 3.850 (s, 2H), 3.750 (s, 3H), 3.610 (s, 3H), 3.487~3.473 (m, 1H), 3.396 (s, 1H), 3.241~3.203 (m, 2H), 3.113 (s, 3H), 3.012~2.768 (m, 6H), 2.566 (s, 3H), 2.532 (s, 1H), 2.383~2.271 (m, 1H), 2.216 (s, 1H), 1.795~1.725 (m, 2H).

Example 2

The Synthesis of Compound (BS-BE-002)

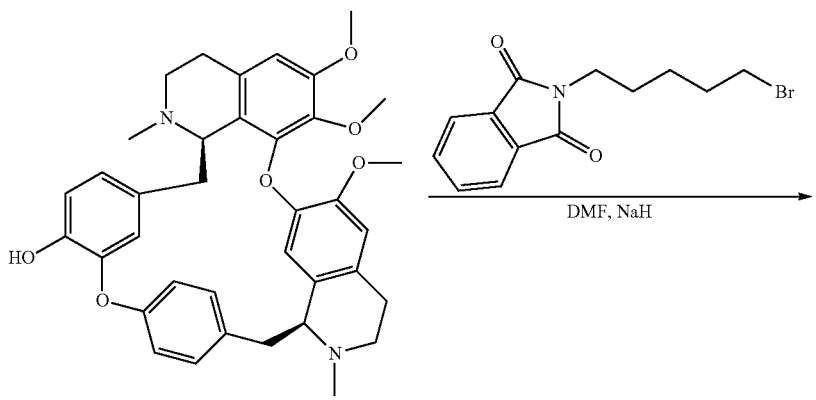

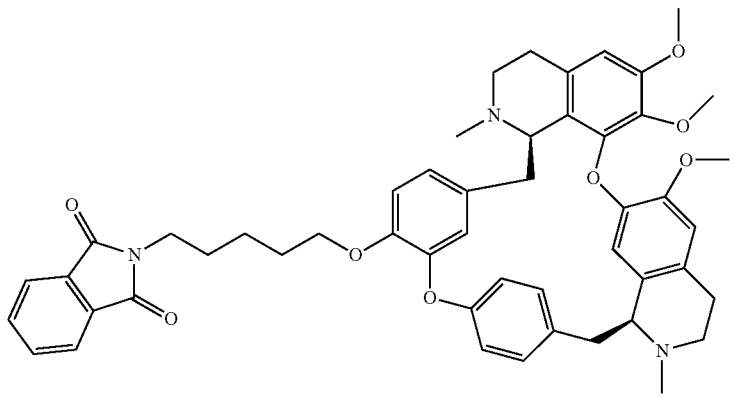

Under a protective nitrogen atmosphere, sodium hydride (NaH, 48 mg, 1.2 mmol) is added into a solution of berbamine dihydrochloride (205 mg, 0.3 mmol) in N,N-dimethyl formamide (5 ml) at 0° C., after being stirred for 1 hour, 2-(5-bromoamyl)-isoindoline-1,3-dione (133 mg, 0.45 mmol) is added therein. The reaction solution is heated to 80° C. overnight. Then the reaction mixture is evaporated under vacuum, and purified by a preparative thin layer chromatography to give white or pale yellow compound (BS-BE-002) (98.4 mg, 39.8%).

LC/MS m/z: M+1 824.2 100% (purity).

$^1$H NMR (CDCl$_3$) δ: 7.826~7.809 (dd, 2H, J=5.5 Hz, 5.5 Hz), 7.692~7.680 (dd, 2H, J=6.0 Hz, 5.5 Hz), 7.26~7.243 (m, 2H), 7.084~7.071 (d, 1H, J=6.5 Hz), 6.79~6.733 (m, 2H), 6.623~6.607 (d, 1H, J=8.0 Hz), 6.529 (s, 1H), 6.395 (s, 1H), 6.272 (s, 1H), 5.971 (s, 1H), 4.069~4.042 (t, 2H, J=6.5 Hz, 7.0 Hz), 3.783 (s, 2H), 3.750 (s, 3H), 3.718~3.689 (t, 2H, J=7.0 Hz, 7.5 Hz), 3.610 (s, 1H), 3.399 (s, 1H), 3.245~3.208 (m, 2H), 3.121 (s, 3H), 3.023~2.779 (m, 6H), 2.569 (s, 3H), 2.540 (s, 1H), 2.370~2.338 (m, 1H), 2.250 (s, 3H), 1.926~1.869 (m, 2H), 1.788~4.682 (m, 3H), 1.570~1.507 (m, 2H).

Example 3

The Synthesis of Compound (BS-BE-003)

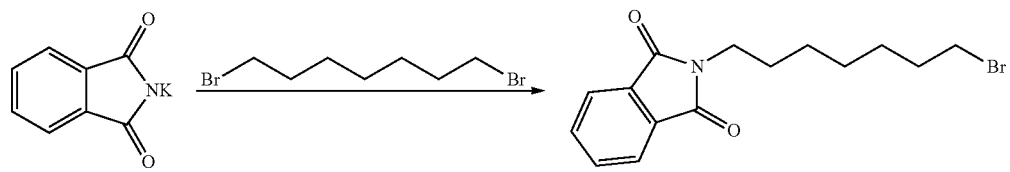

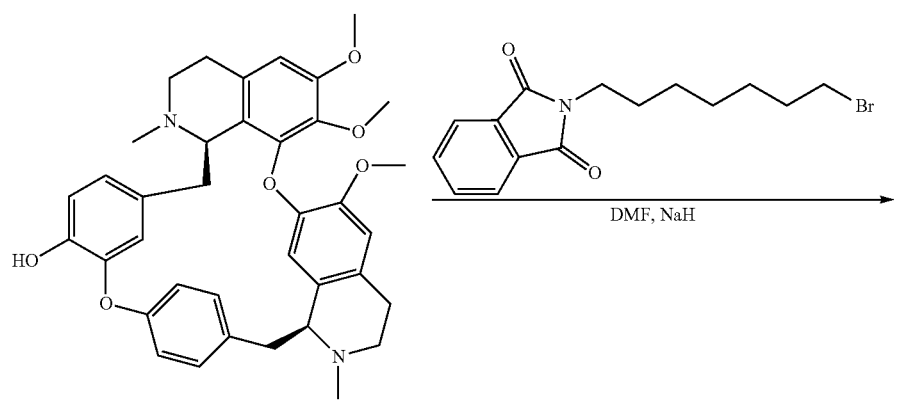

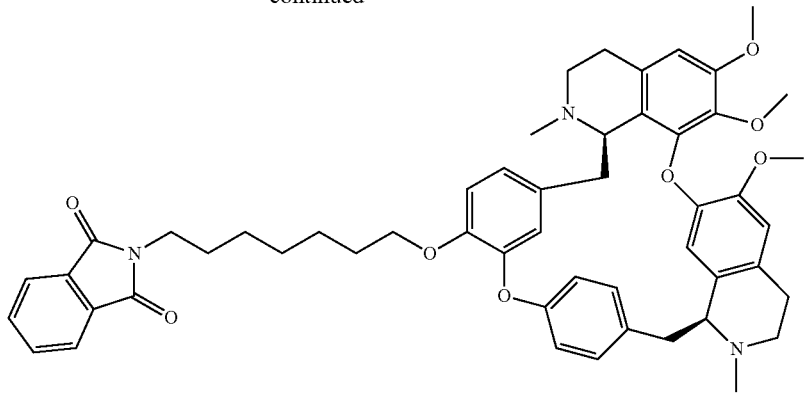

A mixture of 1,7-dibromoheptane and phthalimide potassium (1.0 g, 5.4 mmol) in N,N-dimethyl formamide (8 ml) is heated to 80° C. overnight. After cooling, the reaction mixture is diluted with ethyl acetate (50 mL) and water (50 mL). The organic layer is dried through anhydrous sodium sulfate, and concentrated under vacuum and purified by silica gel column chromatography (1.2 g, 70%).

Under a protective nitrogen atmosphere, sodium hydride (NaH, 48 mg, 1.2 mmol) is added into a solution of berbamine dihydrochloride (205 mg, 0.3 mmol) in N,N-dimethyl formamide (5 ml) at 0° C., after being stirred for 1 hour, 2-(7-bromoheptyl)-isoindoline-1,3-dione (133 mg, 0.45 mmol) is added therein. The reaction solution is heated to 80° C. overnight. Then the reaction mixture is evaporated under vacuum, and purified by a preparative thin layer chromatography to give white or pale yellow compound (BS-BE-003) (20.2 mg, 7.9%).

LC/MS m/z: M+1 852.4 100% (purity).

$^1$H NMR (CDCl$_3$) δ: 7.837~7.820 (dd, 2H, J=5.5 Hz, 5.5 Hz), 7.704~7.687 (dd, 2H, J=6.0 Hz, 5.5 Hz), 7.26~67.247 (m, 1H), 7.099~7.086 (d, 1H, J=6.5 Hz), 6.810~6.753 (m, 2H), 6.625~6.612 (d, 1H, J=6.5 Hz), 6.531 (s, 1H), 6.385 (s, 1H), 6.275 (s, 1H), 5.971 (s, 1H), 4.055~4.028 (t, 2H, J=6.5 Hz, 7.0 Hz), 3.863~3.848 (d, 2H, J=7.5 Hz), 3.750 (s, 3H), 3.679~3.650 (t, 2H, J=7.0 Hz, 7.5 Hz), 3.607 (s, 3H), 3.411 (s, 1H), 3.282~3.213 (m, 2H), 3.122 (s, 3H), 3.043~2.783 (m, 7H), 2.588 (s, 1H), 2.570 (s, 3H), 2.400 (s, 1H), 2.254 (s, 3H), 1.847~1.704 (m, 2H), 1.685~1.657 (m, 2H), 1.481~1.400 (m, 6H).

Example 4

The Synthesis of Compound (BS-BE-004)

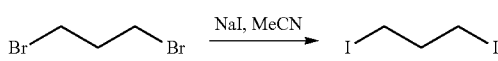

1,3-dibromopropane (1.0 g, 5 mmol) and NaI (3.0 g, 20 mmol) are added into acetonitrile (35 mL), the reaction is heated to 80° C. under stirring for 3 hours to obtain the crude product of 1,3-diiodopropane. This crude product can be used directly for the next step reaction without any purification.

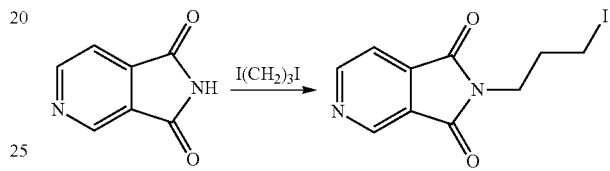

3,4-pyridine-dicarboximide (740 mg, 5 mmol) and K$_2$CO$_3$ (828 mg, 6 mmol) are added into acetonitrile (20 mL), followed by 1,3-diiodopropane (5 mmol) After heated to 80° C., the reaction proceeds for 16 hours. After completion of the reaction, the reaction solution is filtered, then the filtrate is dried by rotary evaporation to obtain a crude product which is purified by column chromatography to get a yellow solid product, N-(3-iodopropyl)-3,4-pyridine-dicarboximide (200 mg, 13%).

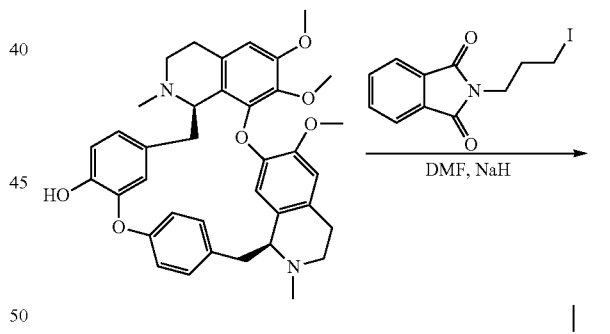

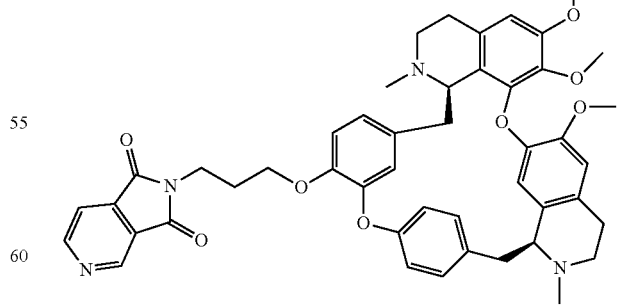

Under a protective nitrogen atmosphere, sodium hydride (NaH, 80 mg, 2 mmol) is added in batch into a solution of berbamine dihydrochloride (305 mg, 0.5 mmol) in N,N-dimethyl formamide (5 ml) at 0° C., after warmed up to room temperature and stirred for 0.5 hour, N-(3-iodopropyl)-3,4-pyridine dicarboximide (160 mg, 0.5 mmol) is added. The reaction solution is heated to 80° C. overnight. After completion of the reaction, the reaction solution is poured into ice water, the crude product obtained through filtration is purified by a preparative thin layer chromatography to get a brown compound (BS-BE-004) (35 mg, 5.0%).

MS m/z: M+1 797.4 LC: 2.835 min (84.99%).

$^1$H NMR (CDCl$_3$) δ: 9.123 (s, 1H), 8.993~8.972 (d, 1H, J=8.4 Hz), 8.194~8.164 (d, 1H, J=8.4 Hz), 7.099~7.084 (d, 1H, J=6.0 Hz), 6.81~6.756 (m, 4H), 6.628~6.613 (d, 1H, J=6.0 Hz), 6.542 (s, 1H), 6.391 (s, 1H), 6.282 (s, 1H), 5.973 (s, 1H), 4.326~3.985 (m, 8H), 3.853~3.132 (m, 2H), 3.752 (s, 3H), 3.702~3.678 (m, 4H), 3.673 (s, 3H), 3.413 (s, 2H), 3.122 (s, 3H), 2.588 (s, 2H), 2.570 (s, 3H), 2.254 (s, 3H), 1.847~1.704 (m, 2H).

Example 5

Evaluation of Anti-Leukemia Activity of the Dicarboximide Derivatives of Berbamine of the Present Invention (1) Experimental Materials Leukemia cell lines: human K562 leukemia cell line (chronic myeloid leukemia, CML), K562/adr (drug-resistant chronic myeloid leukemia (CML), NB4 (acute promyelocytic leukemia, AML), Kasumi-1 (acute myeloid leukemia M2 type, AML-M2), Jurkat (acute lymphoblastic leukemia, ALL), H9 (acute lymphoblastic leukemia, ALL).

Reagents: The berbamine (BBM) standard is purchased from Sichuan Shifang Pukang Biochemistry Limited Company, Sichuan, China.

The berbamine derivatives according to the present invention:
12-O-((1,3-dioxo-isoindolin-2-yl)-methyl)-berbamine (Compound BS-BE-001),
12-O-(5-(1,3-dioxo-isoindolin-2-yl)-pentyl)-berbamine (Compound BS-BE-002),
12-O-(7-(1,3-dioxo-isoindolin-2-yl)-heptyl)-berbamine (Compound BS-BE-003),
12-O-(3-(3,4-pyridine-dicarboximide)-propyl)-berbamine (Compound BS-BE-004).

Main apparatuses: an incubator, and a microplate reader.

(2) Experimental Method

Obtaining 6000 well-growing leukemia cells and inoculating them into wells of a 96-well cell culture plate. The culture medium is the 1640 cell culture medium containing 10% fetal bovine serum. After adding of the berbamine derivatives of different concentrations and mixing uniformly, the plate is placed in a carbon dioxide cell incubator (5% CO$_2$) at 37° C. and incubated for 72 hours. Then the viable cell concentration is determined by the MTT method. In this experiment, the cell viability in control group (not treated with any compound) is set as 100%, and the cell viability (%) after treatment and the 50% inhibiting concentration of the compound for the leukemia cell growth at 72 hours (IC$_{50}$ value of 72 hours) are calculated.

(3) The Experimental Results

The experimental results are shown in table 1. Table 1 demonstrates that the berbamine derivatives of the present invention can induce the death of human chronic myeloid leukemia cells, acute myeloid leukemia cells and acute lymphocytic leukemia cells and inhibit the growth of these leukemia cells. Compared with berbamine itself, the berbamine derivatives of the present invention exhibit significantly enhanced anti-leukemia cell activities, wherein the berbamine derivative (BS-BE-003) of the present invention improves the anti-human K562 chronic myelogenous leukemia activity by more than 5-fold, and improves the anti-K562/adr (drug-resistant chronic myelogenous leukemia) activity by more than 6-fold.

Example 6

Evaluation of the Anti-Human Multiple Myeloma and Lymphoma Cell Activities of the Berbamine Derivatives of the Present Invention (1) Experimental Materials Multiple myeloma and lymphoma cell lines: U266 (multiple myeloma), RPMI8226 (multiple myeloma), and DOHH2 (lymphoma).

Reagent: Same as in Example 5.

Main apparatuses: an incubator, and a microplate reader.

(2) Experimental Method

Obtaining 6000 well-growing aforesaid tumor cells and inoculating them into wells of a 96-well cell culture plate. The culture medium is the 1640 cell culture medium containing 10% fetal bovine serum. After adding the berbamine derivatives of different concentrations and mixing uniformly, the plate is placed in a carbon dioxide cell incubator (5% CO$_2$) at 37° C. and incubated for 72 hours. Then the viable cell concentration is determined by the MTT method. In this experiment, the cell viability of control group (not treated with any compound) is set as 100%, and the cell viability (%) after treatment and the 50% inhibiting concentration of the compound for the leukemia cell growth at 72 hours (IC$_{50}$ value of 72 hours) are calculated.

(3) The Experimental Results

The experimental results are shown in table 1. Table 1 demonstrates that the dicarboximide derivatives of berbamine of the present invention can induce the death of human myeloma and lymphoma cells and inhibit the growth of these tumor cells. Compared with berbamine itself, the anti-myeloma and lymphoma cell activities of the novel berbamine derivatives of the present invention are significantly enhanced, wherein the berbamine derivative (BS-BE-003) of the present invention improves the anti-RPMI8226 (multiple myeloma) cell activity by near 6-fold.

TABLE 1

Determination of half inhibiting concentrations of the dicarboximide derivatives of berbamine on leukemia, lymphoma and multiple myeloma cells (IC$_{50}$ value, 72 hours).

|  | K562 | K562adr | NB4 | Kasumi-1 | Jurkat | H9 | RPMI 8226 |
|---|---|---|---|---|---|---|---|
| BBM | 3 | 3.53 | 3 | 1.3 | 1.9 | 5.04 | 1.17 |
| BS-BE-001 | 0.98 | 0.64 | 1.8 | 3.36 | 1.8 | 2.94 | 0.01 |
| BS-BE-002 |  | 1.02 |  | 1.15 |  | 2.17 |  |

TABLE 1-continued

Determination of half inhibiting concentrations of the dicarboximide derivatives of berbamine on leukemia, lymphoma and multiple myeloma cells (IC$_{50}$ value, 72 hours).

|           | K562 | K562adr | NB4   | Kasumi-1 | Jurkat | H9   | RPMI 8226 |
|-----------|------|---------|-------|----------|--------|------|-----------|
| BS-BE-003 | 0.58 | 0.59    | 0.97  | 1.14     | 0.75   | 1.9  | 0.20      |
| BS-BE-004 | 10   | 5.14    | 16.24 | 9.16     | 9.46   | 7.33 | 3.04      |

Example 7

Evaluation of the Anti-Human Solid Tumor Effect for the Dicarboximide Derivatives of Berbamine of the Present Invention (1) Experimental Materials Human solid tumor cell lines: HepG2 (human hepatocellular carcinoma, HCC), A549 (human lung cancer), MCF-7 (breast cancer), PANC-1 (pancreatic cancer), PC-3 (prostate cancer), MG63 (osteosarcomas), AGS (gastric cancer), Huh7 (human hepatoma cell), Becap37 (human breast cancer cell), Hela (human cervical cancer cell), RKO (human colon adenocarcinoma cell), SW620 (human colon adenocarcinoma cells), SW480 (human colon cancer cell), MGC 803 (human gastric cancer cell).

Reagent: Same as in Example 5.

Main apparatuses: an incubator, and a microplate reader.

(2) Experimental Method

Obtaining 4000 well-growing human solid tumor cells and inoculating them into wells of a 96-well cell culture plate. The culture medium is DMEM High Glucose cell culture medium containing 10% fetal bovine serum. After adding the berbamine derivatives of different concentrations and mixing uniformly, the plate is placed in a carbon dioxide cell incubator (5% $CO_2$) at 37° C. and incubated for 72 hours. Then the viable cell concentration is determined by the MTT method, and the cell viability (%) after drug treatment is calculated. In this experiment, the cell viability of control group (not treated with any compound) is set as 100%.

(3) The Experimental Results

The experimental results are shown in table 2. Table 2 shows that the berbamine derivatives of the present invention can induce the death of human solid tumor cells and inhibit the growth of these tumor cells. Compared with berbamine itself, the berbamine derivatives of the present invention exhibit significantly enhanced anti-human solid tumor cell activities, wherein for the dicarboximide derivatives of berbamine of the present invention (3), the anti-PANC-1 (pancreatic cancer) activity is improved by more than 6-fold, the anti-MCF-7 (breast cancer) activity is improved by near 6-fold, the anti-HepG2 (human hepatocellular carcinoma, HCC) and Becap37 (human breast cancer cell) activities are improved by near 5-fold, the anti-MG63 (osteosarcomas) activity is improved by near 8-fold, and the anti-MGC 803 (human gastric cancer cells) activity is improved by near 7-fold.

TABLE 2

Determination of half inhibiting concentrations of the dicarboximide derivatives of berbamine on human solid tumor cells (IC$_{50}$ value, 72 hours).

|           | MCF-7 | A549 | Huh7 | Hepg2 | Becap 37 | PANC-1 | Hela  |
|-----------|-------|------|------|-------|----------|--------|-------|
| BBM       | 20.56 | 5.38 | 7.63 | 6.67  | 7.31     | 12.72  | 5.04  |
| BS-BE-001 | 9.15  | 4.56 | 5.4  | 5.8   | 5.38     | 6.42   | 3.11  |
| BS-BE-003 | 3.5   | 3    | 3    | 1.56  | 1.54     | 2.06   | 1.49  |
| BS-BE-004 | >16   | >16  | >16  | >16   | 11.37    | >16    | 14.23 |

|           | RKO  | SW620 | SW480 | PC-3 | AGS  | MG63 | MGC803 |
|-----------|------|-------|-------|------|------|------|--------|
| BBM       | 2.34 | 1.1   | 5.74  | 3.7  | 5.84 | 9.18 | 4.96   |
| BS-BE-001 | 2.93 | 1.13  | 4.68  | 3.95 | 3.49 | 4.83 | 2.38   |
| BS-BE-003 | 0.72 | 0.57  | 1.63  | 2.7  | 1.35 | 1.21 | 0.74   |
| BS-BE-004 | 18   | 4.63  | 8.58  | >16  | 8.55 | 16   | 13.5   |

The invention claimed is:

1. A dicarboximide derivative of berbamine of formula (I):

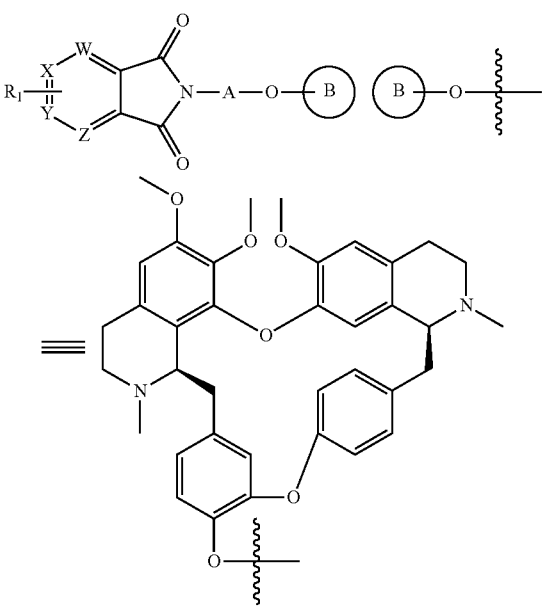

Formula (I)

wherein, $R_1$ is selected from H, halogen, amino, nitro, cyano, hydroxyl, mercapto, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, and substituted or unsubstituted $C_3$-$C_7$ cycloalkyl;

W, X, Y and Z are selected from substituted or unsubstituted methine CH, methylene $CH_2$ and a heteroatom selected from the group consisting of O, N and S, wherein at least two of W, X, Y and Z are CH or $CH_2$;

A is selected from a linear or branched, substituted or unsubstituted alkylene —$(CH_2)_n$—, optionally being interrupted by a heteroatom selected from the group consisting of O, N, and S, wherein when W, X, Y and Z are all CH, n is an integer from 7 to 15, and under the remaining circumstances, n is an integer from 1 to 15;

wherein "substituted" means a substitution by a substituent selected from the group consisting of halogen, amino, nitro, cyano, hydroxyl and mercapto;

or a pharmaceutically acceptable salt thereof.

2. A phthalimide derivative of berbamine of formula (I-a):

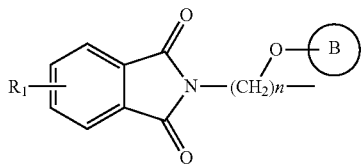

Formula (I-a)

wherein n is an integer of 7-15, and $R_1$ and B are defined same as in formula (I) of claim 1, or a pharmaceutically acceptable salt thereof.

3. An aromatic heterocyclic dicarboximide derivative of berbamine of formula (I-b):

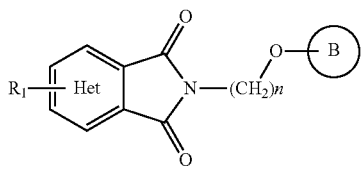

Formula (I-b)

wherein the aromatic heterocyclic group (Het) contains one or two heteroatoms selected from the group consisting of O, N and S, and $R_1$, n and B are defined same as in formula (I) of claim 1, or a pharmaceutically acceptable salt thereof.

4. The dicarboximide derivative of berbamine or a pharmaceutically acceptable salt thereof according to claim 1, wherein n is an integer of 7-10 when W, X, Y and Z are all CH, and under the remaining circumstances, n is an integer of 1-10.

5. The dicarboximide derivative of berbamine or a pharmaceutically acceptable salt thereof according to claim 1, wherein n is an integer of 7-8 when W, X, Y and Z are all CH, and under the remaining circumstances, n is an integer of 1-8.

6. The dicarboximide derivative of berbamine or a pharmaceutically acceptable salt thereof according to claim 1, wherein n is 7 when W, X, Y and Z are all CH, and under the remaining circumstances, n is an integer of 1-7.

7. The dicarboximide derivative of berbamine or a pharmaceutically acceptable salt thereof according to claim 1, wherein $R_1$ is H, $C_1$-$C_6$ alkoxy, $C_1$-$C_6$ alkylthio, $C_1$-$C_6$ alkyl, $C_3$-$C_7$ cycloalkyl, halogen, nitro, cyano or amino optionally substituted with one or two $C_1$-$C_6$ alkyl.

8. The dicarboximide derivative of berbamine or a pharmaceutically acceptable salt thereof according to claim 1, wherein $R_1$ is H, $C_1$-$C_6$ alkoxy, $C_1$-$C_6$ alkyl, $C_3$-$C_7$ cycloalkyl or halogen.

9. The dicarboximide derivative of berbamine or a pharmaceutically acceptable salt thereof according to claim 1, wherein $R_1$ is H, $C_1$-$C_3$ alkoxy, $C_1$-$C_3$ alkyl, or $C_5$-$C_6$ cycloalkyl.

10. The dicarboximide derivative of berbamine or a pharmaceutically acceptable salt thereof according to claim 1, wherein $R_1$ is H, methoxy, or methyl.

11. The dicarboximide derivative of berbamine or a pharmaceutically acceptable salt thereof according to according to claim 1, wherein $R_1$ is H.

12. The dicarboximide derivative of berbamine or a pharmaceutically acceptable salt thereof according to claim 1, selected from the following compounds or a pharmaceutically acceptable salt thereof:

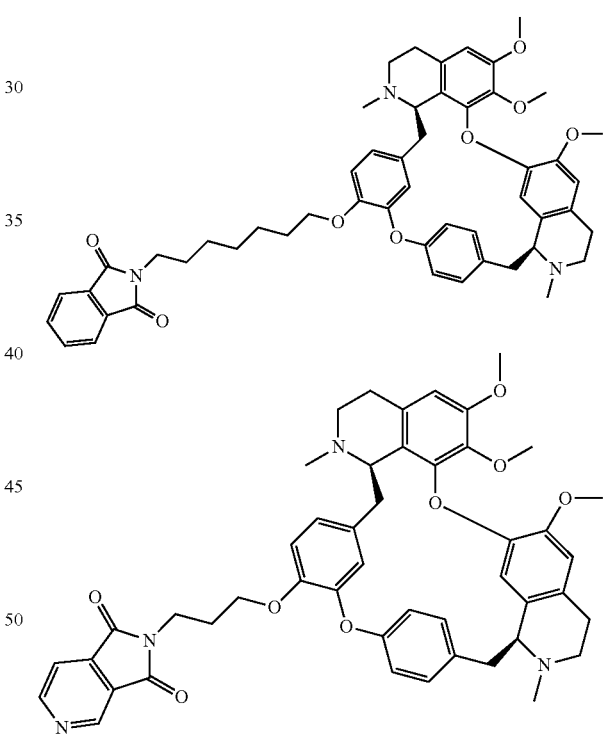

13. A process for preparation of a compound of formula (I),

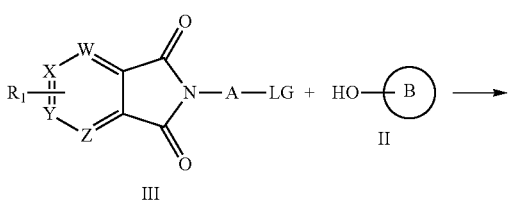

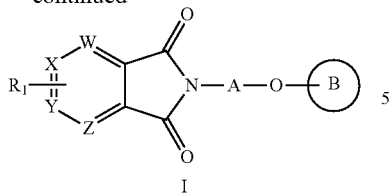

I comprising reacting a compound of formula (III) and a compound of formula (II) to produce a compound of formula (I), wherein A, B, W, X, Y, Z, $R_1$ and n in the compounds of formula (I), (II) and (III) are defined same as in claim 1, and LG is a leaving group.

14. The process according to claim 13, wherein the leaving group LG is a halogen atom or sulfonate group.

15. A pharmaceutical composition comprising the dicarboximide derivative of berbamine or a pharmaceutically acceptable salt thereof according to claim 1 and optionally a pharmaceutically acceptable excipient.

16. A method for treating a patient suffering from tumor, comprising administrating to the patient in need thereof an therapeutically effective amount of the dicarboximide derivative of berbamine or a pharmaceutically acceptable salt thereof according to claim 1, wherein the tumor is selected from leukemia, multiple myeloma, lymphoma, liver cancer, gastric cancer, breast cancer, cholangiocellular carcinoma, pancreatic cancer, lung cancer, carcinoma of large intestine, osteosarcoma, human cervical cancer, glioma, nasopharyngeal carcinoma, laryngeal carcinoma, esophageal cancer, middle ear tumor, melanoma and prostate cancer.

\* \* \* \* \*